(12) United States Patent
Harley

(10) Patent No.: US 7,597,015 B2
(45) Date of Patent: Oct. 6, 2009

(54) PARTICLE SIZE SAMPLER

(75) Inventor: Naomi Harley, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 11/483,129

(22) Filed: Jul. 7, 2006

(65) Prior Publication Data

US 2007/0056390 A1    Mar. 15, 2007

Related U.S. Application Data

(60) Provisional application No. 60/697,831, filed on Jul. 8, 2005.

(51) Int. Cl.
*G01N 15/02* (2006.01)
(52) U.S. Cl. .................. 73/865.5; 73/863.23; 73/28.05
(58) Field of Classification Search ............... 73/865.5, 73/863.22, 863.23, 28.01, 28.04, 28.05
See application file for complete search history.

(56) References Cited

U.S. PATENT DOCUMENTS

| | | | | |
|---|---|---|---|---|
| 3,001,914 A | * | 9/1961 | Andersen | 435/30 |
| 3,983,743 A | * | 10/1976 | Olin et al. | 73/28.06 |
| 4,740,220 A | * | 4/1988 | Mark et al. | 73/863.22 |
| 4,827,779 A | * | 5/1989 | Marple et al. | 73/863.22 |
| 5,333,511 A | * | 8/1994 | Boyum et al. | 73/864.34 |
| 6,284,025 B1 | * | 9/2001 | Kreisberg et al. | 73/28.05 |
| 6,576,045 B2 | * | 6/2003 | Liu et al. | 95/268 |

FOREIGN PATENT DOCUMENTS

SU     421907 A  *  9/1974

* cited by examiner

*Primary Examiner*—Hezron Williams
*Assistant Examiner*—Nashmiya S Fayyaz
(74) *Attorney, Agent, or Firm*—Darby & Darby

(57) ABSTRACT

A particle size sampler includes a cylindrical housing with an inlet end and an outlet end. A pump, connected to an outlet pipe at the outlet end, draws air through the particle size sampler. Aerosols or other particles are removed from the air during a series of filtering steps. The filtering steps include an impactor, a plurality of mesh screens, and a backup filter to remove any particles remaining after the previous filtering steps. The particle size sampler may operate for long periods of time providing a size distribution and concentration of small particles in the air.

23 Claims, 3 Drawing Sheets

PARTICLE SIZE SAMPLER

CROSS-REFERENCE TO RELATED APPLICATIONS

This application claims priority under 35 U.S.C. § 119 to U.S. Provisional Application Ser. No. 60/697,831 filed Jul. 8, 2005, which is hereby incorporated by reference in its entirety.

FIELD OF THE INVENTION

The invention generally relates to an aerosol particle sampler and, more specifically, to a miniature aerosol particle size sampler for measuring a size distribution and concentration of airborne particles.

BACKGROUND

It is well known that airborne pollutants pose serious health risks when inhaled. Depending on the type of particles inhaled, exposure to airborne pollutants over long periods of time can cause serious illness such as asthma, respiratory disease and lung cancer. Therefore, it is desirable to measure the concentration of dangerous inhaled aerosols in areas suspected of having a high concentration of pollutants.

It is also known that the particle size of airborne pollutants determines the location and amount of material deposited in the lung. These two characteristics are critical to the risk of airborne pollutants. Thus, it is not only important to know the concentration of airborne pollutants, but also to know the size distribution of those pollutants.

One device for capturing particles in the air is a cartridge personal sampling impactor as disclosed in U.S. Pat. No. 4,827,779 to Marple et al. which is incorporated herein by reference. The device includes a housing with an impactor and a filter therein. Air is drawn into the device through one or more inlet holes by a pump attached to the outlet of the device. Large particles in the air are removed by the impactor and any remaining particles are contained by the filter for subsequent analysis. Advantages of this device are that it is small, inexpensive and may operate for long periods of time. It may be placed out of the way in a specific area to capture the airborne pollutants in that area or it may be carried by a person to capture all air pollutants encountered by that person. One major drawback of this device is that it cannot produce an integrated size distribution, in other words, a distribution of the concentration of airborne particles based on size over a long period of time.

There are known machines for measuring particle size and air concentration of inhaled aerosol particles in real time, but these machines are expensive. They are also not robust enough for field or outdoor deployment. Typically, the real time measurements provide only short term data and many measurements would be needed to determine if airborne pollutants pose a long term threat in a suspected "risk" area.

Thus, a device for sampling the size distribution of particles in the air which is inexpensive and operates for long periods of time is highly desirable.

SUMMARY OF THE INVENTION

The invention provides a miniature particle size sampler which can operate for long periods of time and in severe weather conditions. The particle sampler may be used to determine the size distribution of any type of airborne particles including radioactive particles, biological species, stable chemicals or elemental substances. It may also be used in any environment such as a nuclear reactor or severe weather. The sampler may be left in one place to determine the size distribution of airborne particles in that environment or may be worn by a person to determine the size distribution of particles encountered by that person.

The miniature particle size sampler includes a housing with an air inlet side and an air outlet side. Within the housing are an impactor, a plurality of mesh screens, and a backup filter arranged in the listed order from the inlet side to the outlet side. In use, the outlet is connected to a low flow pump which draws air through the particle size sampler.

The housing includes a base and an opposing cap. The base includes a substantially flat bottom and a first peripheral wall extending up from a perimeter of the bottom. The cap includes a flat top and a second peripheral wall extending down from a perimeter of the top. The cap is attached to the base such that the first peripheral wall abuts the second peripheral wall creating an enclosure inside the walls and the top and bottom of the housing. The cap and base may include tabs with holes disposed therein such that screws or bolts can be used to attach the cap and base. Preferably, a seal is formed where the peripheral wall of the cap meets the peripheral wall of the base.

The inlet end of the housing includes at least one inlet hole and the outlet end includes an outlet. The outlet may include a pipe extending outward from the particle size sampler designed to fit a hose or tube that is attached to a pump. Additionally, the outlet may include a channel within the particle size sampler such that air is drawn through the outlet from a center of the outlet end.

The first stage of the particle size sampler is an impactor stage. An impactor plate as is known in the art is held within the particle size sampler a predetermined distance from the inlet hole perpendicular to the air flow. The impactor stage is used to separate large particles out of the air stream. In use, air is brought down into the particle size sampler through the inlet hole. Larger particles continue on their downward path until they collide with the impactor plate where they stick and remain. In contrast, smaller particles are swept with the air through a hole in the impactor plate. A preferred embodiment uses an impactor stage with a size cutoff of approximately 1 to 3 microns.

The second stage includes at least one mesh screen. The screen captures particles from the air that are below the cutoff size of the impactor. The size of the mesh determines a penetration efficiency curve based on particle size such that the screen has a greater chance of capturing particles of one size but a lower chance of capturing particles of another size. A plurality of mesh screens may be used in the particle size sampler each screen having characteristics to capture a certain sized particle. This embodiment separates the airborne particles into a set size distribution. A preferred embodiment includes six mesh screens, each including stainless steel mesh.

The final stage of the particle size sampler is a backup filter which removes any residual particles from the air. The particles caught by the backup filter are those residual particles remaining in the air flow. After the backup filter stage, the particle-free air is drawn out of the particle size sampler.

BRIEF DESCRIPTION OF THE DRAWINGS

These and other objects and features of the invention will become more apparent by referring to the drawings, in which:

FIG. 1b is a perspective view of the particle size sampler shown in FIG. 1a;

DETAILED DESCRIPTION OF THE PREFERRED EMBODIMENTS

Figure 1A:
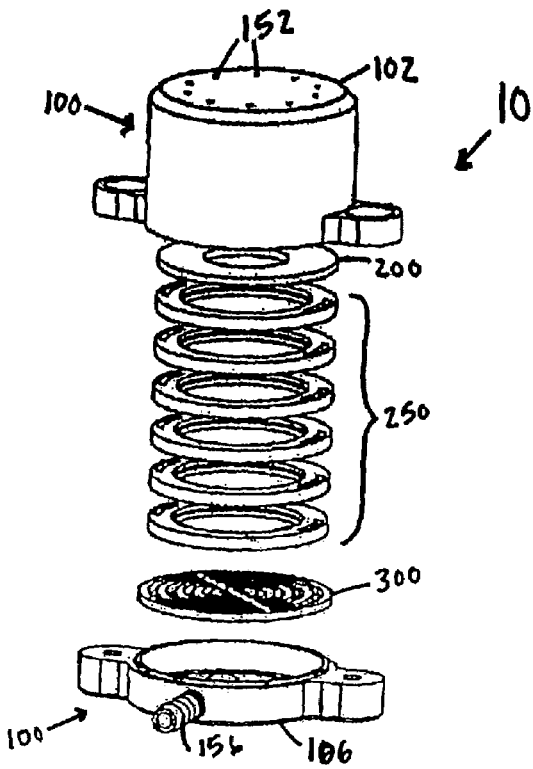
FIG. 1a is an exploded view of a particle size sampler in accordance with the present invention.
Figure 1B:
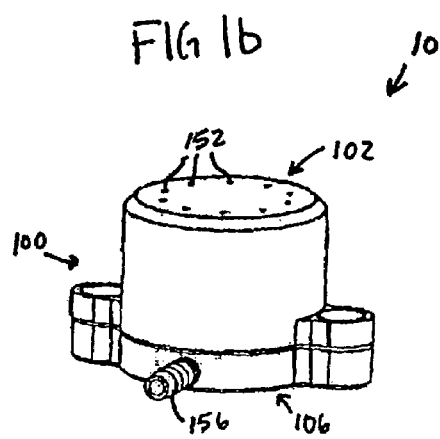

Miniature particle size sampler 10 is shown in FIG. 1a and FIG. 1b. Particle size sampler 10 includes housing 100 with an air inlet side 102 including a plurality of inlet holes 152 and an air outlet side 106 with air outlet 156. Within housing 100 are impactor 200, a plurality of mesh screens 250, and backup filter 300 arranged in the listed order from inlet side 102 to outlet side 106 of particle size sampler 10. In use, air outlet 156 is connected to a low flow pump (not shown) which draws air through particle size sampler 10.

Figure 2A:
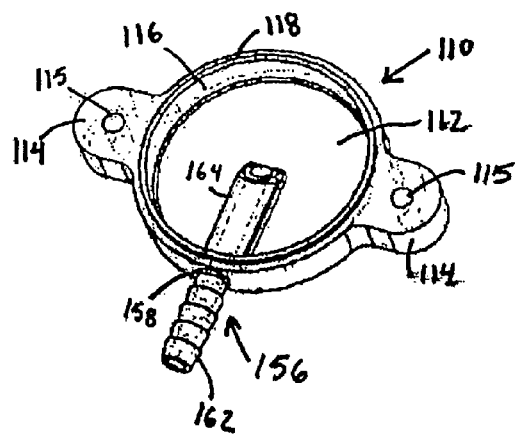
FIGS. 2a and 2b are perspective views of the housing base and cap, respectively.
Figure 2B:
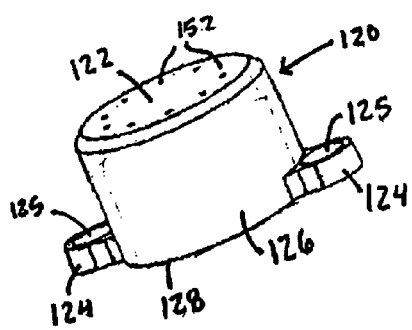

Housing 100 may be formed of any stiff material which will not be easily bent or damaged, such as metal or plastic. In a preferred embodiment, housing 100 is formed of electrically neutral plastic including embedded nickel coated carbon fibers. Housing 100 is generally cylindrical with a round base 110 and an opposing round cap 120 as shown in FIG. 2a and FIG. 2b, respectively. Base 110 includes a flat bottom 112 and a first peripheral wall 116 extending up from a perimeter of bottom 112. Cap 120 includes a flat top 122 and a second peripheral wall 126 extending down from a perimeter of top 122. First peripheral wall 116 includes an upper edge 118 and second peripheral wall 126 includes a lower edge 128.

Cap 120 is attached to base 110 such that upper edge 118 of first peripheral wall 116 is adjacent lower edge 128 of second peripheral wall 126. In a preferred embodiment base 110 and cap 120 each include opposing tabs 114 and 124, respectively. Tabs 114 and 124 include holes 115 and 125, respectively, such that base 110 and cap 120 may be attached using bolts or screws through holes 115 and 125. Holes 115 and 125 may be threaded and/or countersunk. Base 110 and cap 120 should be attached such that a seal is formed where upper edge 118 meets lower edge 128 and no air leaves housing 100 except through air outlet 156.

Cap 120 includes a plurality of small inlet holes 152 disposed toward the perimeter of top 122. Base 110 includes outlet 156 including a hole 158 allowing air out of the particle size sampler 10. The hole 158 may be placed in first peripheral wall 116. A pipe 162 may extend from hole 158 outwardly from base 110. The pipe 162 is designed to fit a tube or hose (not shown) thereon by any method as is well known in the art. A channel 164 in communication with pipe 162 may extend inward from first peripheral wall 116 to the center of bottom 112 such that air may be drawn through particle size sampler 10 symmetrically by way of channel 164 and pipe 162.

Figure 3:
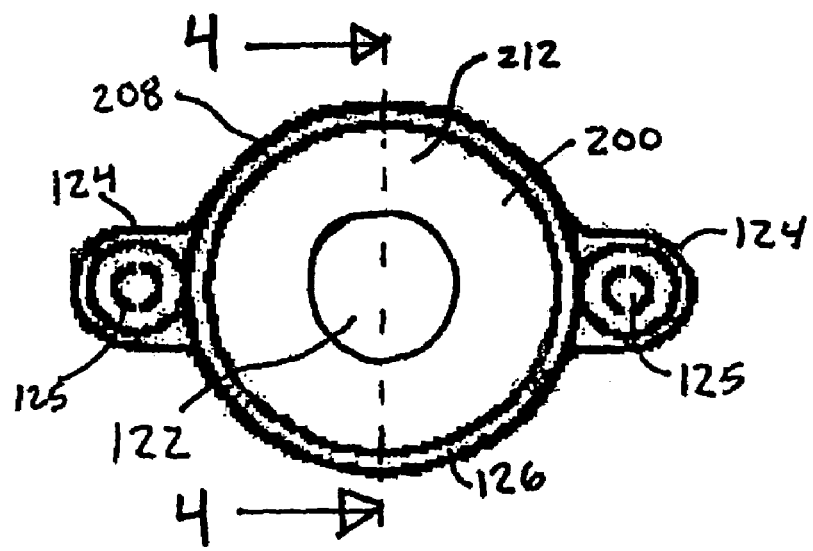
FIG. 3 is a front view of the housing cap.
Figure 4:
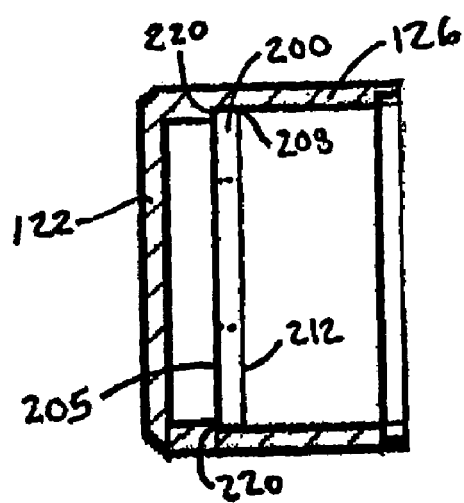
FIG. 4 is a cross section of the housing cap of FIG. 3 taken along line 4-4.

The first stage of the particle size sampler 10 is an impactor stage. An impactor ring 200 is disposed near inlet end 102 in spaced apart relationship from top 122. As shown in FIGS. 3 and 4, a top side 205 of impactor ring 200 abuts a ledge 220 along second peripheral wall 126. An outer edge 208 of impactor ring 200 is adjacent and concentric with second peripheral wall 126. Ledge 220 holds impactor ring 200 a predetermined distance from top 122 of cap 120. The impactor stage is used to separate large particles and some ultra-fine particles out of the air stream. Air is brought down into particle size sampler 10 through inlet holes 152. Larger particles continue on their downward path until they collide with impactor ring 200. In contrast, smaller particles are swept through impactor ring 200 with the air. A washer (not shown) may be included between impactor ring 200 and cap 120 to prevent air from flowing around impactor ring 200 rather than through it. The surface 212 of impactor ring 200 may include a porous material or a coating to help attach the large particles to impactor 200. The surface 212 of impactor ring 200 may also include a medium for direct counting of radioactivity. The size of the particles removed during the impactor stage is determined by the distance between impactor ring 200 and cap top 122 and by the velocity of the inlet air. For example, these parameters may be set to yield an impactor cutoff size between 1 and 3 microns.

Figure 5A:
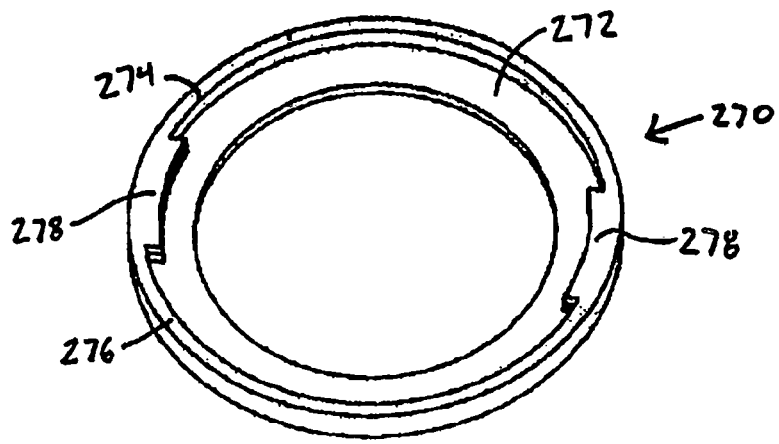
FIGS. 5a-5c are perspective views of the outer ring, inner ring and mesh circle, respectively, of a mesh screen of the particle size sampler.
Figure 5B:
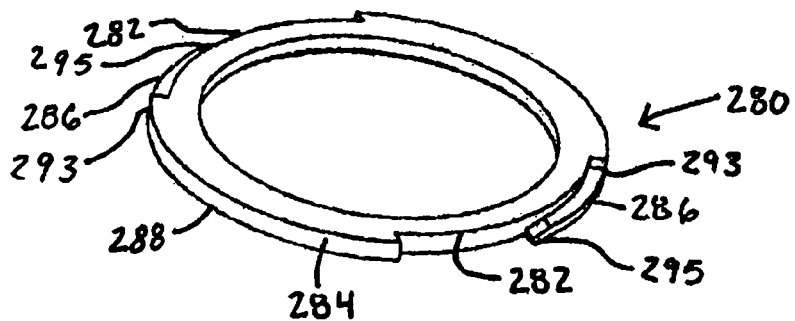
Figure 5C:
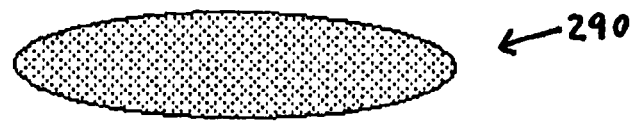

After the impactor stage the air flows through a series of finer and finer mesh screens 250. Each mesh screen 250 collects particles of different sizes depending on the particles' penetration efficiency through the screen. The penetration efficiency is determined by the size of the mesh 290 such that screens of different sizes are more likely to capture particles of a certain size. Each mesh screen 250 includes an outer ring 270, an inner ring 280, and a circle of mesh 290 as shown in FIGS. 5a, 5b and 5c. Outer ring 270 includes base 272 and outer ridge 274. One or more overhangs 278 extend inward from the top 276 of outer ridge 274. Inner ring 280 includes one or more cutout sections 282 on an outer edge 284 thereof. Within cutout section 282, a projection 286 extends outward from a bottom 288 of inner ring 280. In a preferred embodiment projection 286 is inclined such that the height of projection 286 is larger at a first end 293 than it is at a second end 295. In a preferred embodiment the circle of mesh 290 is formed of stainless steel.

To assemble mesh screen 250, the mesh 290 is placed in outer ring 270 on base 272 concentric with outer ridge 274. Inner ring 280 is then placed within outer ring 270 by passing overhang 278 through cutout section 282. Inner ring 280 is then rotated with respect to outer ring 270 until projection 286 is beneath overhang 278 and circle of mesh 290 is held firmly between outer ring 270 and inner ring 280. Inclined projection 286 allows various mesh sizes to be used with inner ring 280 and outer ring 270. If a relatively thick circle of mesh 290 is used inner ring 280 only needs to be rotated slightly until circle of mesh 290 is held firmly. On the other hand, if a very thin circle of mesh 290 is used, inner ring 280 may be rotated further until circle of mesh 290 is firmly held in place. Friction prevents inner ring 280 from rotating and allowing it to fall out of outer ring 270.

The final stage of particle size sampler 10 is backup filter 300, which removes any residual particles from the air. A thin filter cloth or the like may be supported by a disk with holes to make up backup filter 300. The air is then removed from the particle size sampler 10 through air outlet 156.

As the air flows through particle size sampler 10 the largest particles are successively removed until no particles remain in the air when it passes through outlet 156. The largest particles are initially caught by the impactor. Subsequently, the first screen 250 captures any particles larger than its mesh size but below the impactor cutoff size. The remaining screens 250 each captures any particles between the size of its mesh 290 and the size of the preceding screen's mesh 290. Finally, any residual particles are removed by the backup filter 300. After use, the impactor 200, backup filter 300 and each screen 250 contain particles of a different size creating a size and concentration distribution of the particles. The particles may then be further analyzed by methods well known in the art.

The particle size sampler may be used to measure concentrations of any aerosol particulates including biological, chemical and radioactive particles. The particle size sampler may be used for long periods of time, typically operating for several months. It may be used as an area sampler but is small enough that it may also be attached and carried by a person. Thus, the particle size sampler is able to operate continuously and produce a size distribution of airborne particles over long periods of time.

Although the preferred form of the invention has been shown and described, many features may be varied, as will readily be apparent to those skilled in this art. Thus, the foregoing description is illustrative and not limiting.

I claim:

1. A particle size sampler comprising:
   a housing having
      a base formed as a unitary structure and including an outlet, a bottom and a first peripheral wall, and
      a cap formed as a unitary structure and including an inlet end and a second peripheral wall, the base being attached to the cap;
   an impactor positioned within the housing and proximate the inlet end;
   a filter positioned within the housing and proximate the outlet end; and
   a first mesh screen configured to capture particles thereon and positioned within the housing between the impactor and filter, wherein the capture particles are separated according to size.

2. The particle size sampler according to claim 1 further comprising a second mesh screen between the first mesh screen and the filter, the second mesh screen being finer than the first mesh screen.

3. The particle size sampler according to claim 1 further comprising a plurality of additional mesh screens, the first mesh screen and plurality of additional mesh screens arranged such that the screens are progressively finer from the inlet side to the outlet side.

4. A particle size sampler comprising:
   a housing defining an inlet side, an outlet side and an air flow path therethrough;
   an impactor positioned within the housing and proximate the inlet side;
   a first mesh screen configured to capture particles thereon positioned within the housing, abutting a wall of the housing, and extending substantially across the entire flow path; and
   a second mesh screen configured to capture articles thereon positioned within the housing, abutting a wall of the housing, and extending substantially across the entire flow path,
   wherein the air flow path travels from the first mesh screen to the second mesh screen substantially along an axial direction, and wherein the captured particles are separated according to size.

5. The particle size sampler of claim 1 wherein the cap includes a flat top with a plurality of inlet holes.

6. The particle size sampler of claim 1 wherein the impactor includes an impactor ring disposed a predetermined distance from the inlet side.

7. The particle size sampler of claim 6 wherein a surface of the impactor ring is at least one of porous or coated.

8. The particle size sampler of claim 6 wherein a surface of the impactor ring is suitable for measuring radioactivity.

9. The particle size sampler of claim 1 wherein the impactor has a particle size cutoff between 1 and 3 micrometers.

10. The particle size sampler of claim 6 wherein the housing includes a radial projection that holds the impactor ring at the predetermined distance from the inlet side.

11. The particle size sampler of claim 6 wherein a particle size cutoff of the impactor is determined by the predetermined distance.

12. The particle size sampler of claim 1 wherein the housing is formed of electrically neutral plastic including embedded nickel coated carbon fibers.

13. The particle size sampler of claim 1 wherein the base and cap each include at least one tab for attaching to each other.

14. The particle size sampler of claim 1 wherein the filter includes a filter cloth supported by a disk including at least one hole therein.

15. The particle size sampler of claim 1 wherein the mesh screen comprises:
   an inner ring;
   an outer ring; and
   mesh held between the inner ring and outer ring.

16. A particle size sampler comprising:
   a housing having an inlet side and an outlet side;
   an impactor positioned within the housing and proximate the inlet side;
   a filter positioned within the housing and proximate the outlet side; and
   a first mesh screen positioned within the housing between the impactor and filter, the mesh screen comprising:
   an outer ring including:
      a base,
      an outer ridge extending up from the base, and
      an overhang extending inward from the outer ridge;
   an inner ring including:
      a cutout section on an outer edge thereof, and
      a projection extending outward and within the cutout section; and
   mesh held between the base and inner ring, wherein the projection is disposed under the overhang to hold the inner ring and outer ring together.

17. The particle size sampler of claim 16, wherein the projection is inclined to accommodate mesh of various thickness.

18. The particle size sampler of claim 15, wherein the inner and outer ring may be adjusted relative to each other to accommodate mesh of various thickness.

19. A particle size sampler comprising:
   a housing defining an inlet side, an outlet side and an air flow path therethrough;
   an impactor positioned within the housing and proximate the inlet side; and
   a plurality of mesh screens configured to capture particles thereon, each mesh screen positioned within the housing, abutting a wall of the housing, and extending substantially across the entire flow path, the mesh screens having different capturing efficiencies, wherein the captured particles are separated according to size.

20. The particle size sampler of claim 19 further comprising a filter within the housing and proximate the outlet side.

21. A method of making a particle size sampler comprising the steps of:
   placing an impactor ring in spaced apart relation from an inlet side of a particle size sampler housing and within the housing abutting a wall of the housing;

placing a plurality of mesh screens configured to capture particles thereon within the housing abutting a wall of the housing, the mesh screens having different capturing efficiencies;

placing a filter within the housing; and closing the housing, wherein the captured particles are separated according to size.

22. The method of claim 21 further comprising the step of arranging the plurality of mesh screens such that each of the plurality of mesh screens includes a screen that is finer than an adjacent one of the plurality of mesh screens that is closer to the inlet side.

23. The method of claim 21 further comprising the step of assembling each mesh screen by placing a circle of mesh between an inner ring and an outer ring.

* * * * *